United States Patent [19]

Sweeney

[11] Patent Number: 4,915,786

[45] Date of Patent: Apr. 10, 1990

[54] NONIONIC EMULSIFIER AND SUBSTITUTED SUCCINIC ANHYDRIDE COMPOSITONS THEREWITH

[75] Inventor: W. Alan Sweeney, Larkspur, Calif.

[73] Assignee: Chevron Research Company, San Francisco, Calif.

[21] Appl. No.: 909,979

[22] Filed: Sep. 22, 1986

Related U.S. Application Data

[60] Continuation of Ser. No. 638,169, Aug. 6, 1984, abandoned, which is a division of Ser. No. 449,324, Dec. 13, 1982, abandoned.

[51] Int. Cl.$^4$ .............................................. D21H 3/08
[52] U.S. Cl. ..................................... 162/158; 162/179; 427/384; 427/394; 427/395
[58] Field of Search ............................... 162/158, 179; 106/287.2, 287.23, 287.24; 252/310, 311; 427/384, 394, 395

[56] References Cited

U.S. PATENT DOCUMENTS

| | | | |
|---|---|---|---|
| 3,821,069 | 6/1974 | Wurzburg | 162/179 |
| 3,968,310 | 7/1976 | Stowell | 428/411 |

FOREIGN PATENT DOCUMENTS

| | | |
|---|---|---|
| 74619 | 3/1983 | European Pat. Off. . |
| 107199 | 5/1984 | European Pat. Off. . |
| 896376 | 5/1962 | United Kingdom . |
| 1087635 | 10/1967 | United Kingdom . |
| 1588067 | 4/1981 | United Kingdom . |

*Primary Examiner*—Peter Chin
*Attorney, Agent, or Firm*—C. J. Caroli; R. C. Gaffney

[57] ABSTRACT

An emulsifier comprising the reaction product of a substituted succinic anhydride and a nonionic water-soluble compound having 1 to 3 reactive polar groups. There is also disclosed a stable substituted succinic anhydride/nonionic emulsifier composition, a method for imparting water repellency to surfaces containing groups reactive to anhydrides, and a method for the sizing of paper using said composition.

21 Claims, No Drawings

NONIONIC EMULSIFIER AND SUBSTITUTED SUCCINIC ANHYDRIDE COMPOSITONS THEREWITH

This is a continuation of application Ser. No. 638,169, filed Aug. 6, 1984, now abandoned, which is a division of Ser. No. 449,324, filed Dec. 13, 1982, now abandoned.

BACKGROUND OF THE INVENTION

It is well known in the art that hydrocarbyl-substituted succinic anhydrides are good for treating paper, fabric, or other surfaces to impart water repellency. As indicated in U.S. Pat. Nos. 3,102,064, 3,821,069, 3,968,005, and 4,040,900 (RE 29,960), these compositions are particularly useful for sizing paper.

It is also known that these succinic anhydrides are best applied for such purposes in a highly dispersed form, such as an aqueous emulsion. See, for example, U.S. Pat. No. 4,040,900 (RE 29,960), which describes paper sizing emulsions made from mixtures comprising a substituted cyclic dicarboxylic acid anhydride and polyoxyalkylene alkyl or alkylaryl ether or the corresponding mono- and di-ester.

U.S. Pat. No. 3,968,310 describes half-ester reaction products obtained by reacting maleated alphaolefins with hydrocarbylpolyoxyalkylene alkanols. These half-ester reaction products are useful as hot melt adhesives for paper stocks. However, these compositions suffer the disadvantage of being insoluble in water at neutral or acidic pH and are ineffective in forming aqueous emulsions.

SUMMARY OF THE INVENTION

The present invention provides a novel nonionic emulsifier comprising the reaction product of:

(a) a hydrocarbyl-substituted succinic anhydride having from 6 to 50 carbon atoms in the substituent; and (b) a nonionic water-soluble compound having from 1 to 3 reactive polar groups, wherein said water-soluble compound has sufficient hydrophilic strength to give a balanced oil-in-water emulsifier;

and wherein the emulsifier so produced contains a free carboxyl group and a substituted carboxyl group per each reacted anhydride molecule.

The invention further provides a stable hydrocarbyl-substituted succinic anhydride/nonionic emulsifier composition comprising 70 to 99.5% of a normally liquid hydrocarbyl-substituted succinic anhydride having from 6 to 50 carbon atoms in the substituent and 0.5 to 30% of the emulsifier described above.

The present invention is also concerned with a method of imparting water repellency to surfaces containing groups reactive to anhydrides which comprises impregnating said surfaces with an aqueous emulsion of the substituted succinic anhydride/nonionic emulsifier composition of the invention.

The present invention is further concerned with a method of sizing paper which comprises intimately dispersing within the wet paper pulp, prior to the ultimate conversion of said pulp into a dry web, an aqueous emulsion of the substituted succinic anhydride/nonionic emulsifier composition of the invention.

Among other factors, the present invention is based on my discovery that certain half-ester reaction products of substituted succinic anhydride are found to be superior emulsifiers which are surprisingly unaffected by changes in water hardness and pH.

An additional advantage of the present invention is the fact that these emulsifiers can be combined with substituted succinic anhydride to provide stable mixtures which are highly effective in treating various surfaces to impart water repellency. These compositions are particularly useful as superior paper sizing agents.

DETAILED DESCRIPTION OF THE INVENTION

The substituted succinic anhydride useful for this invention is a hydrophobic molecule. Usually it will have one substituent in the 3-position but it may have substituents in both the 3- and 4-positions. In general, the substituents will be an alkyl, alkenyl or aralkyl group. Other elements may be present in a minor amount, such as sulfur or ether linkage. The total number of carbon atoms in the substituent is between 6 and 50. A preferred substituent size is between 10 and 30. More preferred is between 12 and 25. A preferred embodiment of the contemplated anhydrides is the alkenyl succinic anhydride made by allowing an olefin to react with maleic anhydride. For the present purposes, I shall refer to the anhydrides contemplated as "ASA".

The nonionic water-soluble compound suitable for use can have incorporated a wide variety of polar groups such as amino, amine oxide, hydroxyl, ether, sulfoxide, sulfhydryl, nitro, and the like, to impart water solubility. It must also contain at least one and not more than three groups which will react with the anhydride to produce an ester, amide, or similar linkage, and a free carboxyl group. The number of polar groups must be proportional to the number of reactive groups so that sufficient hydrophilicity is present to balance all the ASA molecules which react. Polyhydric molecules such as sugars are not suitable.

The nonionic water-soluble compound can readily contain small alkyl or alkylene groups in the $C_1$ to $C_4$ range. It can also contain larger alkyl groups as long as the overall molecule has high hydrophilicity. Such molecules would have a hydrophobic-hydrophilic balance outside the normal surfactant/emulsifier range and would be termed "solubilizers".

A particularly useful type of nonionic water-soluble reactant is the polyethylene glycol or polyoxyethylene class of compounds. This class of compounds is well known in the art and is discussed, for example, in U.S. Pat. No. 3,697,438, the disclosure of which is incorporated herein by reference. As described above, these compounds are suitable when they can balance the hydrophobic nature of the ASA. The number of ethylene oxide units can range from about 4 to 50. When two free hydroxyls are present, the number of ethylene oxide units needed will be higher, from about 8 to 100. Lower alkyl or alkylene groups may also be present such as that obtained by capping one end with methyl or ethyl or by incorporating some propylene or butylene glycol. A large detergent range hydrophobic alkyl, acyl or alkylaryl group may only be present if it is overbalanced by a large surplus of polyoxyethylene groups.

Representative examples of the polyethylene glycol class of compounds include polyethylene glycol 1000 (PEG 1000) and methoxy polyethylene glycol 550 (MPG 550). The number which appears after the polyethylene glycol in the above designation represents the degree of polymerization of the polyethylene glycol.

More specifically, the number appearing in the designation "polyethylene glycol 1000" indicates that the number of ethylene oxide units in the polymeric compound are such as to yield a total average molecular weight of about 1000. Similarly, methoxy polyethylene glycol 550 has a total average molecular weight of about 550.

The novel emulsifiers of the present invention have wide utility in various applications as wetting agents, detergents or emulsifiers. They are water-soluble, giving stable oil-in-water emulsions. As noted previously, these novel emulsifiers contain free carboxyl groups. These carboxyl groups add hydrophilicity to the molecule. When the emulsifier is used in any aqueous medium, these carboxyl groups may be partially ionized, depending on the pH. Surprisingly, the presence of these carboxyl groups does not hinder emulsifier behavior in hard water or when the pH is changed. The present emulsifiers, as a class, can be either foaming or nonfoaming in use.

The hydrophobic/hydrophilic balance is in the normal emulsifier-detergent range. One way of defining this balance is by the use of the HLB scale (Hydrophile-Lipophile Balance). See P. Becker, Chapter 18, in "Nonionic Surfactants", M. J. Schick, Editor, Marcel Dekker (1967). On that scale, for my oil-in-water emulsifiers, the HLB should be about 9–16. The HLB is difficult to estimate for the generalized embodiment of the present emulsifiers. However, when, according to this invention, the hydrophilic moiety is polyethylene glycol, it is believed that HLB can be estimated by:

$$HLB = \frac{E + C}{5}$$

where E equals the weight percent of the oxyethylene content, and C equals the weight percent of the free carboxyl, which also adds hydrophilic character to the molecule.

For example, with an ASA of molecular weight 350 reacting with a methoxy polyethylene glycol 550, E equals 61% and C equals 5%. HLB equals 13.

In addition to obtaining good emulsifier properties by keeping the HLB below about 16, good solubility at room temperature in the material to be emulsified is desired. For solubility in ASA, the molecular weight of the polyethylene glycol moiety should not be over about 4000.

This emulsifier is easier to prepare than most nonionic emulsifiers. It can be prepared under relatively mild conditions without a catalyst and without needing to handle gaseous, noxious ethylene oxide. The reactants, ASA and the hydrophilic compound are simply mixed and allowed to react. The hydrophilic reactant should be dry so that anhydride hydrolysis is avoided. A catalyst may be added but it is preferred to conduct the reaction by simple heating. With most hydrophilic reactants, such as the polyethylene glycols, heating for several hours at 80° to 150° C. is satisfactory. For other more or less reactive hydrophilic reactants, the temperature needed may range from room temperature to about 250° C. The ratio of reactants will be close to an equivalent basis, i.e., one anhydride group for each reactive group on the hydrophile. The subsequent emulsifier use may determine when it is suitable to have some excess of the ASA or of the hydrophilic reagent.

One particularly attractive use for the novel emulsifiers is in emulsifying ASA in water prior to using the ASA to treat various surfaces to impart water-repellency. Herein is described new ASA/emulsifier mixtures which incorporate this new emulsifier and which are superior to those in the art. These ASA/emulsifier combinations are easy to make at a central location, store and ship to the location where the ASA emulsions will be made.

In general, these novel ASA/emulsifier compositions comprise a mixture of:

(a) 70 to 99.5% of a normally liquid hydrocarbyl-substituted succinic anhydride containing between 6 and 50 carbon atoms in the substituent; and (b) 0.5 to 30% of an emulsifier comprising the reaction product of a hydrocarbyl-substituted succinic anhydride containing between 6 and 50 carbon atoms in the substituent and a nonionic water-soluble compound or compounds, each containing 1 to 3 reactive polar groups, said water-soluble compound having sufficient hydrophilic strength to give a balanced oil-in-water emulsifier;

and wherein the emulsifier so produced has a substituted carboxyl group and a free carboxyl group per each reacted anhydride.

The two components are miscible and the mixture is liquid at ambient temperatures. It may be prepared by first making the emulsifier composition and dissolving it in the anhydride ("ASA"). In this way, a different ASA may be used for the emulsifier preparation than that used to make the ASA/emulsifier composition. When different ASA's are not needed, a preferred method is to add a very small amount of the emulsifier hydrophilic reactant to the ASA and make the ASA/emulsifier mixture all in one step. Roughly the same time and temperature are required as would be when making the emulsifier separately. The hydrophilic reactant should be dry so that anhydride hydrolysis is avoided. A catalyst may be added but it is preferred to conduct the reaction by heating in the range of 50° to 250° C. as is done when making the emulsifier separately. The amount of hydrophilic compound added is calculated to give the desired mixture of ASA and emulsifier after reaction of the hydrophilic compound with a minor part of the ASA. For example, when 5% of methoxy polyethylene glycol 550 is added to a $C_{18}$ ASA (M.W. 350), 3.2% of the ASA is reacted and the final mixture contains 8.2% emulsifier. Mixtures of hydrophilic reactants may also be employed.

This ASA/emulsifier composition readily emulsifies into water of various hardness and pH with simple mixing in the absence of high shear. Fine droplets are formed and the emulsion is stable until it is used for treating a surface which contains groups reactive to the anhydride. The time between formation and use could range from a few seconds to several hours. Longer times are generally not preferred because the anhydride groups will gradually be hydrolyzed by the water present.

The water used can be relatively pure or can contain the usual impurities in domestic water. It can have a pH above or below 7, generally in the range of 3 to 11. Calcium and magnesium hardness ions may be present.

The amount of ASA suspended in the water can vary widely, from a few parts per million to 10% or more depending on the use and method of application. For wood or fabric treatment, concentrations around 1% may be used, whereas for internal paper sizing, the concentration in the pump slurry is normally below about 100 parts per million. Thereby about 0.1 to 1% of ASA is finally absorbed on the paper.

Surfaces to be treated with the ASA/emulsifier compositions of the invention to gain water repellency will contain integral groups which are reactive to the ASA anhydride group. This normally will involve reaction with groups such as hydroxyl, amino or mercapto. A preferred type of material which may be treated with emulsions of the compositions of the invention contains carbohydrate molecules, such as cellulose or starch, at the surface of the material. These materials contain many hydroxyl groups which can react with the ASA.

As stated above, the ASA/emulsifier compositions of the present invention may be used to impart water repellency to cellulosic materials. The water-repellent compositions described above are preferably applied to the material in aqueous emulsions. The emulsion may be sprayed onto the material or the material may be dipped into the emulsion in order to distribute the derivative evenly throughout the material. The impregnated material is then withdrawn from the solution and air dried. After air drying, the material is then heated, preferably to a temperature in excess of 100° C., to effect a curing of the impregnated agent within the material. It has been found that one may conveniently use a temperature of about 125° C. for a period of 15 to 20 minutes. At lower temperatures, longer periods of time are required to effect the curing process. To be commercially practical, the curing time should be as short as possible and generally less than one hour. At higher temperatures, the heat curing may be accomplished in shorter periods of time. The upper limit of temperature at which the heat curing process may be carried out is limited to the temperatures at which the cellulosic material begins to decompose. Using the composition of the present invention, it is preferred to impregnate the material with from about 0.5 to 3% by weight of the material of the ASA/emulsifier composition.

The ASA/emulsifier compositions of the present invention may additionally be used as paper sizing agents. These novel sizing agents display all of the features and advantages of prior at sizing agents. Moreover, the novel sizing agents of this invention impart to paper sized therewith a particularly good resistance to acidic liquids such as acid inks, citric acid, lactic acid etc. as compared to paper sized with the sizing agents of the prior art. In addition to the properties already mentioned, these sizing agents may also be used in combination with alum as well as with any of the pigments, fillers and other ingredients which may be added to paper. The sizing agents of the present invention may also be used in conjunction with other sizing agents so as to obtain additive sizing effects. A still further advantage is that they do not detract from the strength of the paper and when used with certain adjuncts will, in fact, increase the strength of the finished sheets. Only mild drying or curing conditions are required to develop full sizing value.

The actual use of these sizing agents in the manufacture of paper is subject to a number of variations in technique any of which may be further modified in light of the specific requirements of the practitioner. It is important to emphasize, however, that with all of these procedures, it is most essential to achieve a uniform dispersal of the sizing agent throughout the fiber slurry, in the form of minute droplets which can come in intimate contact with the fiber surface. Uniform dispersal may be obtained by adding the sizing agent to the pulp or by adding a previously formed, fully dispersed emulsion. Chemical dispersing agents may also be added to the fiber slurry.

Another important factor in the effective utilization of the sizing agents of this invention involves their use in conjunction with a material which is either cationic in nature or is, on the other hand, capable of ionizing or dissociating in such a manner as to produce one or more cations or other positively charged moieties. These cationic agents, as they will be hereinafter referred to, have been found useful as a means for aiding in the retention of sizing agents herein as well as for bringing the latter into close proximity to the pulp fibers. Among the materials which may be employed as cationic agents in the sizing process, one may list alum, aluminum chloride, long chain fatty amines, sodium aluminate, substituted polyacrylamide, chromic sulfate, animal glue, cationic thermosetting resins and polyamide polymers. Of particular interest for use as cationic agents are various cationic starch derivatives including primary, secondary, tertiary or quaternary amine starch derivatives and other cationic nitrogen substituted starch derivatives, as well as cationic sulfonium and phosphonium starch derivatives. Such derivatives may be prepared from all types of starches including corn, tapioca, potato, waxy maize, wheat and rice. Moreover, they may be in their original granule form or they may be converted to pregelatinized, cold water soluble products.

Any of the above noted cationic agents may be added to the stock, i.e., the pulp slurry, either prior to, along with, or after the addition of the sizing agent. However, in order to achieve maximum distribution, it is preferable that the cationic agent be added either subsequent to or in direct combination with the sizing agent. The actual addition to the stock of either the cationic agent or the sizing agent may take place at any point in the paper making process prior to the ultimate conversion of the wet pulp into a dry web or sheet. Thus, for example, these sizing agents may be added to the pulp while the latter is in the headbox, beater, hydropulper or stock chest.

Further improvements in the water resistance of the paper prepared with these novel sizing agents may be obtained by curing the resulting webs, sheets, or molded products. This curing process involves heating the paper at temperatures in the range of from 80° to 150° C. for periods of from 1 to 60 minutes. However, it should again be noted that post curing is not essential to the successful operation of this invention.

The sizing agents of this invention may, of course, be successfully utilized for the sizing of paper prepared from all types of both cellulosic and combinations of cellulosic with non-cellulosic fibers. The cellulosic fibers which may be used include bleached and unbleached sulfate (kraft), bleached and unbleached sulfite, bleached and unbleached soda, neutral sulfite, semichemical chemiground-wood, ground wood, and any combination of these fibers. These designations refer to wood pulp fibers which have been prepared by means of a variety of processes which are used in the pulp and paper industry. In addition, synthetic fibers of the viscose rayon or regenerated cellulose type can also be used.

All types of pigments and fillers may be added to the paper which is to be sized with the novel sizing agents of this invention. Such materials include clay, talc, titanium dioxide, calcium carbonate, calcium sulfate, and diatomaceous earths. Other additives, including alum, as well as other sizing agents, can also be used with these sizing agents.

With respect to proportions, the sizing agents may be employed in amounts ranging from about 0.5 to about 3.0% of the dry weight of the pulp in the finished sheet or web. While amounts in excess of 3% may be used, the benefits of increased sizing properties are usually not economically justified. Within the mentioned range the precise amount of size which is to be used will depend for the most part upon the type of pulp which is being utilized, the specific operating conditions, as well as the particular end use for which the paper is destined. Thus, for example, paper which will require good water resistance or ink holdout will necessitate the use of a higher concentration of sizing agent than paper which does not.

The following examples are provided to illustrate the invention in accordance with the principles of this invention but are not to be construed as limiting the invention in any way except as indicated by the appended claims.

EXAMPLES

Example 1

The alkenyl succinic anhydride (ASA) used in this experiment was a commercially available product made from maleic anhydride and a $C_{15-20}$ straight-chain olefin mixture. Roughly equal amounts of each carbon number are present and the double bond position in the starting olefin mixture was almost all internal. The average molecular weight corresponds to about 17.4 carbons in the olefin mixture.

The ASA (12.0 g, 0.0351 moles) was mixed with methoxy polyethylene glycol 550 (16.08 g, 0.0292 moles) and heated at 80° C. for 14 hours. Infrared analysis showed that the reaction was near completion: hydroxyl and anhydride absorptions fell while ester and carboxyl absorptions grew. NMR and IR analyses were consistent with this structure for the product:

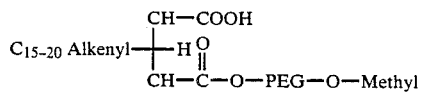

A minor amount (about 7) of excess ASA is also still present.

This product dissolves readily in water at the 0.1% level giving a clear, foaming solution. When 0.1% of a 5% mixture of this product in 50/50 chloroform/n-hexadecane was shaken in water, an emulsion was formed.

Example 2

Using the ASA of Example 1 (10.0 g, 0.0292 moles), a similar nonionic surfactant was made from polyethylene glycol 1000 (12.18 g, 0.0122 moles) by heating for 12 hours at 120° C. NMR and IR analyses were consistent with this structure for the product:

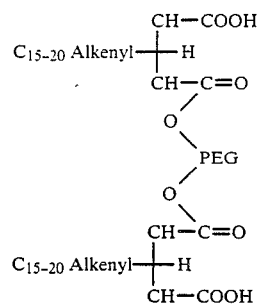

Example 3

The emulsifier composition of Example 1 was used to make an ASA/emulsifier composition which readily emulsifies in water. Nine percent of the emulsifier from Example 1 was dissolved in the ASA described in Example 1. This mixture readily formed an emulsion in water at the 0.1 level when simply shaken by hand.

Example 4

The emulsifier composition of Example 2 was used to make an ASA/emulsifier composition which readily emulsifies in water. Nine percent of the emulsifier from Example 2 was dissolved in the ASA described in Example 1. This mixture readily formed an emulsion in water at the 0.1% level when simply shaken by hand.

Example 5

As a simpler procedure for making the ASA/emulsifier composition of Example 3, only 5% of methoxy polyethylene glycol 550 was added to the ASA of Example 1 and heated at 80° C. for 140 minutes. Similar changes to those observed in Example 1 were seen in NMR and IR spectra. The final product readily emulsified in water. See Table 1.

Example 6

As a simpler procedure for making the ASA/emulsifier composition of Example 4, only 5% of polyethylene glycol 1000 was added to the ASA of Example 1 and heated at 80° C. for 140 minutes. Similar changes to those seen in Example 2 were seen in NMR and IR spectra. The final product readily emulsified in water. See Table 1.

Example 7

Two experiments were made as in Example 6 except that in one case (a) 2.5% of polyethylene glycol 1000 and in the other (b) 10% of polyethylene glycol 1000 was employed. Heating was for 18 hours at 120° C. These products readily emulsified in water. See Table 1.

Example 8

The relative emulsifying power of several different ASA/emulsifier combinations was checked using a simple test. One drop (0.026 g) of the test mixture was shaken vigorously in 25 ml of water for 15 seconds. Emulsion homogeneity was observed and turbidity measurements were made on the Klett-Summerson Colorimeter using standard ½-inch colorimeter test tubes and a No. 42 blue filter. Turbidity Klett readings of about 400–600 indicate excellent emulsions. Readings below about 150 indicate very poor emulsion formation.

The Klett measurements and visual observations were translated into a qualitative emulsion stability ranking scale as follows:

|  | Klett Reading, Fresh | Behavior on Standing up to 24 hours |
|---|---|---|
| Excellent | >400 | No change |
| Good | >300 | Slight separation in 24 hours |
| Fair | >200 | Definite separation in 24 hours |
| Poor | >100 | Definite separation in 2-3 hours |

Ineffective: Incomplete emulsification when fresh

The results are listed in Table 1. They show that compositions of the present invention produce excellent emulsions, equal to or better than commercial emulsifiers. The emulsions from Examples 5 and 6 were so stable they did not change appreciably after standing for 1 month.

Notice that the Examples 5 and 6 compositions did not form any stable foam, whereas some of the ASA mixtures with commercial emulsifiers did.

TABLE 1

| Emulsion Tests of ASA[1]/Emulsifier Mixtures Freshly Made | | | |
|---|---|---|---|
|  | Amount of Emulsifier % | Emulsion Rating | Foam After 30 minutes |
| ASA alone | 0 | No emulsion | None |
| ASA + Commercial Emulsifiers | | | |
| Igepal CO-630 | 10 | Excellent | 1½ ml |
|  | 7 | Excellent |  |
| Tergitol TMN-6 | 10 | Fair |  |
| PEG 400 Monooleate | 10 | Excellent | None |
| PEG 600 Dilaurate | 10 | Good | 1½ ml |
| New ASA Compositions | | | |
| Example 5 | 8 | Excellent | None |
| Example 6 | 8½ | Excellent | None |
| Example 7(a) | 4 | Good |  |
| (b) | 17 | Excellent |  |

[1]ASA described in Example 1.

Example 9

The ASA/emulsifier combinations of Example 8 were tested to see if they maintained their emulsifiability on standing. They were kept at room temperature for a number of days or given an accelerated aging by heating for a number of hours at 80° C. One hour at 80° C. was roughly equal to 3 days at room temperature. The results are shown in Table 2. They show that the mixtures of ASA with the commercial emulsifiers have very poor storage stability and would have to be used freshly mixed. The products of the present invention are quite stable.

TABLE 2

| Storage Stability of ASA[1]/Emulsifier Mixtures | | | |
|---|---|---|---|
|  | Amount of Emulsifier % | Storage | Emulsion Rating |
| ASA + Commercial Emulsifiers | | | |
| Igepal CO-630 | 7 | 3 days at R.T. | Poor |
|  |  | 7 days at R.T. | Ineffective |
|  | 10 | 1 hour at 80° C. | Poor |
| Tergitol TMN-6 | 10 | 1 hour at 80° C. | Poor |
| PEG 400 Monooleate | 10 | 1 hour at 80° C. | Poor |
| PEG 600 Dilaurate | 10 | 1 hour at 80° C. | Fair |

TABLE 2-continued

| Storage Stability of ASA[1]/Emulsifier Mixtures | | | |
|---|---|---|---|
|  | Amount of Emulsifier % | Storage | Emulsion Rating |
| New ASA Compositions | | | |
| Example 5 | 8 | 71 days at R.T. | Excellent |
| Example 6 | 8½ | 17 days at R.T. | Excellent |

[1]ASA described in Example 1.

Example 10

The procedure of Examples 5 and 6 was followed except that other methoxy polyethylene glycol (MPG) reactants were substituted for MPG 550 and other polyethylene glycols (PEG) reactants for PEG 1000.

In addition, other types of hydrophilic compounds were included. Two small hydrophiles, methoxyethoxyethanol, having only two ether oxygens, and 1,3-bis(-dimethylamino)-2-propanol were tested. On the other hand, molecules having much larger hydrophobic segments than the methyl group in the MPG's, but which still have an overwhelming hydrophilic character, were also tested.

The test results are shown in Table 3. These results show that, to make an effective emulsifier:

(1) the molecular weight must be above about 200 in the MPG series and above about 400 in the PEG series;

(2) a broad range of molecular weights is effective in both the MPG and PEG series;

(3) the optimum molecular weight is between about 350 and 1500 in the MPG series and about 700 and 3000 in the PEG series;

(4) fewer polar groups are needed in the hydrophile when ether groups are replaced by dimethylamino groups; and (5) when the polyethylene glycol component is large enough, the hydrophile can contain hydrophobic groups as large as the usual surfactant hydrophobes.

TABLE 3

| Reaction of ASA[1] With Various Hydrophiles | | | |
|---|---|---|---|
| Hydrophilic Reactant | Amount Added (%) | Reaction Conditions | Emulsion Rating |
| MPG 350 | 5 | 140 minutes at 80° C. | Excellent |
| MPG 750 | 5 | 140 minutes at 80° C. | Excellent |
| MPG 1900 | 5 | 17 hours at 120° C. | Good |
| MPG 5000 | 5 | 17 hours at 120° C. | Not tested, solid ppt. in product |
| PEG 400 | 5 | 140 minutes at 80° C. | Ineffective |
| PEG 600 | 5 | 3 hours at 80° C. | Good |
| PEG 600 | 5 | 8 hours at 80° C. | Poor |
| PEG 1540 | 5 | 8 hours at 120° C. | Excellent |
| PEG 4000 | 5 | 8 hours at 120° C. | Good |
| Methoxyethoxyethanol (M.W. 120) | 5 | 17 hours at 120° C. | Ineffective |
| 1,3-bis(dimethylamino)-2-propanol | 10 | 1 hour at 80° C. | Good |
| PEG 4000 monolaurate | 10 | 16 hours at 120° C. | Excellent |
| PEG 4000 monostearate | 10 | 2 hours at 150° C. | Not all soluble |

TABLE 3-continued

Reaction of ASA[1] With Various Hydrophiles

| Hydrophilic Reactant | Amount Added (%) | Reaction Conditions | Emulsion Rating |
|---|---|---|---|
| t-octyl phenol/40 EO | 10 | 2 hours at 150° C. | Fair |

[1] ASA described in Example 1.

Example 11

The procedure of Example 6 was followed except that various ASA compounds were used separately in place of the ASA described in Example 1. Heating with 5% PEG 1000 was for 17 hours at 120° C. The ASA's used were:

(1) a branched ASA derived from tetrapropylene;
(2) a branched ASA derived from hexapropylene;
(3) isooctadecyl ASA;
(4) isooctadecenyl ASA; and
(5) a $C_{20}$ ASA derived from a dimer of $C_{10}$ straight-chain alpha olefin.

In each case, an excellent emulsion was formed when tested by the method of Example 8.

Example 12

The ASA/emulsifier composition of Example 6 was tested as in Example 8 but using a variety of aqueous conditions as follows:

(1) Distilled water, pH 6.3
(2) Tap water (about 50 ppm hardness), pH 8.7
(3) Synthetic hard water-180 ppm hardness, pH 7.2
(4) pH 4 buffer solution
(5) pH 10 buffer solution In each of these cases, good-to-excellent emulsions were obtained. A test was also made in a synthetic seawater (30,000 ppm hardness) where a poor emulsion was obtained. In addition, an emulsion of the Example 6 composition was made in which the concentration of ASA in water was 10%. A thick, milky emulsion readily formed which showed only minor creaming on standing.

Example 13

Three simple water-repellency demonstrations were made to show the efficacy of the ASA/emulsifier composition of Example 6. Pieces of cotton denim, redwood shingle and paper towels were treated with the 0.1% water emulsion, dried, and cured at 120° to 150° C. for 1 to 2 hours. In each case, the treated material was compared with untreated material by dropping a stream of water on the surface of each. In each case, the water immediately penetrated the untreated material, whereas water did not penetrate the treated sample for 10 seconds or more.

What is claimed is:

1. A method of imparting water repellency to surfaces containing groups reactive to anhydrides which comprises impregnating said surfaces with an aqueous emulsion of a stable hydrocarbyl-substituted succinic anhydride/nonionic emulsifier composition comprising:
  (a) 70 to 99.5% of a normally liquid hydrocarbyl-substituted succinic anhydride having from 10 to 30 carbon atoms in the substituent; and
  (b) 0.5 to 30% of a water-soluble emulsifier comprising the reaction product of a hydrocarbyl-substituted succinic anhydride having from 10 to 30 carbon atoms in the substituent and a nonionic water-soluble compound having 1 to 3 groups reactive to anhydrides, wherein said water-soluble compound has sufficient hydrophilic strength to give a balanced oil-in-water emulsifier;

and wherein the emulsifier so produced contains a free carboxyl group and a substituted carboxyl group per each reacted anhydride molecule.

2. The method according to claim 1, wherein said surfaces are cellulosic materials.

3. The method according to claim 1, wherein the hydrocarbyl substituents of components (a) and (b) are independently selected from the group consisting of alkyl, alkenyl and aralkyl.

4. The method according to claim 3, wherein the hydrocarbyl substituents of components (a) and (b) are alkenyl.

5. The method according to claim 1, wherein the hydrocarbyl substituents of components (a) and (b) each contain from 12 to 25 carbon atoms.

6. The method according to claim 1, wherein the water-soluble compound further contains polar groups independently selected from the group consisting of amino, amine oxide, hydroxyl, ether, sulfoxide, sulfhydryl, and nitro.

7. The method according to claim 1, wherein the water-soluble compound is a polyethylene glycol or alkoxy polyethylene glycol.

8. The method according to claim 7, wherein the water-soluble compound is a methoxy polyethylene glycol.

9. The method according to claim 1, wherein the emulsifier of component (b) has a hydrophobic/hydrophilic balance in the range of about 9 to 16 on the HLB scale.

10. The method according to claim 1, wherein the succinic anhydride of components (a) and (b) is an alkenyl succinic anhydride derived from maleic anhydride and olefins in the $C_{10}$ to $C_{30}$ range and the water-soluble compound of component (b) is a methoxy polyethylene glycol having a molecular weight of about 550.

11. The method according to claim 1, wherein the succinic anhydride of components (a) and (b) is an alkenyl succinic anhydride derived from maleic anhydride and olefins in the $C_{10}$ to $C_{30}$ range, and the water-soluble compound of component (b) is a polyethylene glycol having a molecular weight of about 1000.

12. A method of sizing paper which comprises the step of intimately dispersing within the wet pulp, prior to the ultimate conversion of said pulp into a dry web, an aqueous emulsion of a stable hydrocarbyl-substituted succinic anhydride/nonionic emulsifier composition comprising:
  (a) 70 to 99.5% of a normally liquid hydrocarbyl-substituted succinic anhydride having from 10 to 30 carbon atoms in the substituent; and
  (b) 0.5 to 30% of a water-soluble emulsifier comprising the reaction product of a hydrocarbyl-substituted succinic anhydride having from 10 to 30 carbon atoms in the substituent and a nonionic water-soluble compound having 1 to 3 groups reactive to anhydrides, wherein said water-soluble compound has sufficient hydrophilic strength to give a balanced oil-in-water emulsifier;

and wherein the emulsifier so produced contains a free carboxyl group and a substituted carboxyl group per each reacted anhydride molecule.

13. The method according to claim 12, wherein the hydrocarbyl substituents of components (a) and (b) are independently selected from the group consisting of alkyl, alkenyl and aralkyl.

14. The method according to claim 13, wherein the hydrocarbyl substituents of components (a) and (b) are alkenyl.

15. The method according to claim 12, wherein the hydrocarbyl substituents of components (a) and (b) each contain from 12 to 25 carbon atoms.

16. The method according to claim 12, wherein the water-soluble compound further contains polar groups independently selected from the group consisting of amino, amine oxide, hydroxyl, ether, sulfoxide, sulfhydryl, and nitro.

17. The method according to claim 12, wherein the water-soluble compound is a polyethylene glycol or alkoxy polyethylene glycol.

18. The method according to claim 17, wherein the water-soluble compound is a methoxy polyethylene glycol.

19. The method according to claim 12, wherein the emulsifier of component (b) has a hydrophobic/hydrophilic balance in the range of about 9 to 16 on the HLB scale.

20. The method according to claim 12, wherein the succinic anhydride of components (a) and (b) is an alkenyl succinic anhydride derived from maleic anhydride and olefins in the $C_{10}$ to $C_{30}$ range and the water-soluble compound of component (b) is a methoxy polyethylene glycol having a molecular weight of about 550.

21. The method according to claim 12, wherein the succinic anhydride of components (a) and (b) is an alkenyl succinic anhydride derived from maleic anhydride and olefins in the $C_{10}$ to $C_{30}$ range, and the water-soluble compound of component (b) is a polyethylene glycol having a molecular weight of about 1000.

* * * * *